United States Patent
Li et al.

(10) Patent No.: US 9,610,238 B2
(45) Date of Patent: *Apr. 4, 2017

(54) NAIL COMPOSITIONS

(71) Applicant: L'OREAL, Paris (FR)

(72) Inventors: Chunhua Li, Scotch Plains, NJ (US); Hy Si Bui, Piscataway, NJ (US); Jean-Thierry Simonnet, Mamaroneck, NY (US)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/649,441

(22) PCT Filed: Dec. 5, 2012

(86) PCT No.: PCT/US2012/067930
§ 371 (c)(1),
(2) Date: Jun. 3, 2015

(87) PCT Pub. No.: WO2014/088568
PCT Pub. Date: Jun. 12, 2014

(65) Prior Publication Data
US 2015/0342863 A1 Dec. 3, 2015

(51) Int. Cl.
*A61K 8/87* (2006.01)
*A61K 8/40* (2006.01)
*A61Q 3/02* (2006.01)
*A61K 8/81* (2006.01)

(52) U.S. Cl.
CPC .............. *A61K 8/87* (2013.01); *A61K 8/8152* (2013.01); *A61Q 3/02* (2013.01); *A61K 2800/43* (2013.01); *A61K 2800/54* (2013.01); *A61K 2800/81* (2013.01); *A61K 2800/884* (2013.01)

(58) Field of Classification Search
CPC .. A61K 2800/81; A61K 2800/95; A61K 8/37; A61K 8/87; A61Q 3/02
See application file for complete search history.

(56) References Cited

U.S. PATENT DOCUMENTS

| | | | |
|---|---|---|---|
| 6,197,316 B1 * | 3/2001 | Ellingson | A61K 8/731 424/401 |
| 6,391,964 B1 | 5/2002 | Tartaglia | |
| 6,471,950 B1 | 10/2002 | Farer et al. | |
| 7,837,742 B2 | 11/2010 | Morrissey et al. | |
| 7,998,222 B2 | 8/2011 | Morrissey et al. | |
| 2010/0260687 A1 | 10/2010 | Yu et al. | |
| 2011/0033401 A1 | 2/2011 | Morrissey et al. | |
| 2011/0060065 A1 * | 3/2011 | Vu | A61K 8/8152 521/149 |
| 2011/0150805 A1 * | 6/2011 | Kergosien | A61K 8/04 424/70.7 |
| 2015/0265524 A1 * | 9/2015 | Li | A61K 8/8117 424/61 |
| 2015/0342863 A1 * | 12/2015 | Li | A61Q 3/02 132/200 |

FOREIGN PATENT DOCUMENTS

WO 2012/061267 A2 5/2012

OTHER PUBLICATIONS

International Search Report with Written Opinion issued Aug. 20, 2013 in PCT/US2012/067930 filed Dec. 5, 2012.
U.S. Appl. No. 14/649,368, filed Jun. 3, 2015, Li, et al.
U.S. Appl. No. 14/416,438, filed Jan. 22, 2015, Li, et al.

* cited by examiner

*Primary Examiner* — Anna Falkowitz
(74) *Attorney, Agent, or Firm* — Oblon, McClelland, Maier & Neustadt, L.L.P.

(57) ABSTRACT

The invention relates to nail composition sets comprising at least one primer comprising compound(s) other than acrylic latex and at least one color coat comprising at least one acrylic latex and water.

12 Claims, No Drawings

NAIL COMPOSITIONS

FIELD OF THE INVENTION

The present invention relates to nail compositions comprising (1) at least one color coat comprising acrylic latex and water and (2) at least one primer based on compound(s) other than acrylic latex. The primer reduces and/or inhibits staining of the nails by the color coat.

DISCUSSION OF THE BACKGROUND

Traditional water-based nail enamels can result in nails being stained after removal of the enamels from the nails. Typically, such water-based enamels contain water-soluble dyes as colorants. Staining can result from the water-soluble dyes penetrating into the nail and staining the nail.

In the past, attempts have been made to modify the colorant in such nail enamels to render the colorant insoluble in water. Such attempts include converting the colorants to lakes, and using the colorants in such form in nail enamel products. However, in the presence of water or other solubilizing solvents, it is still possible for the colorant to solubilize and stain nails to which the enamel has been applied. Further attempts to solve the staining problem have included surface treating and/or encapsulating colorant. Representative examples of such attempts include U.S. Pat. Nos. 6,528,044, 6,471,950, 5,599,530, 5,139,570, 4,832, 944, and 4,344,932, and U.S. patent applications 2011/0033401 and 2006/0171909.

There remains a need for nail enamel compositions which are safe and adhere well to nails, yet which result in less staining to nails after removal from the nails.

SUMMARY OF THE INVENTION

The present invention relates to a nail composition set comprising at least one color coat comprising acrylic latex and water, and at least one primer based on compound(s) other than acrylic latex.

The present invention also relates to a nail composition set comprising at least one color coat comprising acrylic latex and water, and at least one primer based on at least one polyurethane.

The present invention further relates to a nail composition set comprising (1) at least one color coat comprising acrylic latex and water, (2) at least one primer based on compound(s) other than acrylic latex, and (3) optionally at least one topcoat.

The present invention further relates to a nail composition set comprising (1) at least one color coat comprising acrylic latex and water, (2) at least one primer based on at least one polyurethane, and (3) optionally at least one topcoat.

The present invention further relates to methods for making up and/or protecting nails comprising applying to the nails at least one color coat comprising at least one acrylic latex and water, and at least one primer based on compound(s) other than acrylic latex. Preferably, the at least one primer is based on at least one polyurethane.

The present invention further relates to methods for making up and/or protecting nails comprising applying to the nails (1) at least one color coat comprising at least one acrylic latex and water, (2) at least one primer based on compound(s) other than acrylic latex, and (3) optionally at least one topcoat. Preferably, the at least one primer is based on at least one polyurethane.

The present invention further relates to methods of inhibiting a color coat comprising at least one acrylic latex and water from staining a nail to which the color coat is applied comprising applying to the nail at least one primer based on compound(s) other than acrylic latex prior to applying the color coat to the nail. Preferably, the at least one primer is based on at least one polyurethane.

It is to be understood that both the foregoing general description and the following detailed description are exemplary and explanatory only, and are not restrictive of the invention.

DETAILED DESCRIPTION OF THE INVENTION

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% to 15% of the indicated number.

"Film former" or "film forming agent" as used herein means a polymer or resin that leaves a film on the substrate to which it is applied, for example, after a solvent accompanying the film former has evaporated, absorbed into and/or dissipated on the substrate.

"Makeup Result" as used herein, refers to compositions where color remains the same or substantially the same as at the time of application, as viewed by the naked eye, after an extended period of time. "Makeup Result" may be evaluated by evaluating long wear properties by any method known in the art for evaluating such properties. For example, long wear may be evaluated by a test involving the application of a composition to nails and evaluating the color of the composition after an extended period of time. For example, the color of a composition may be evaluated immediately following application to nails and these characteristics may then be re-evaluated and compared after a certain amount of time. Further, these characteristics may be evaluated with respect to other compositions, such as commercially available compositions.

"Adhesion" as used herein, refers to chemical or physical bonding between a coating and a substrate. Good adhesion between nail polish and nail surface should translate to good wear properties on consumers. Adhesion properties can be quantified by in-vitro method such as a cross-cut adhesion test. In the test, a lattice pattern is cut into the coating and penetrates through to the substrate. A pressure sensitive tape is applied to the sample and then pulled off. The adhesion property can be quantified by the area of the coating remaining after peeling. For example, if the whole film remains after peeling, it indicates excellent adhesion. If most of the film gets peeled off, it indicates poor adhesion. The cross-cut test is an industrial standard test for testing adhesion for coatings. (Reference # ISO/DIN 2409, ASTM D3359).

"Substituted" as used herein, means comprising at least one substituent. Non-limiting examples of substituents for substitution include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Volatile", as used herein, means having a flash point of less than about 100° C.

"Non-volatile", as used herein, means having a flash point of greater than about 100° C.

The compositions and methods of the present invention can comprise, consist of, or consist essentially of the essential elements and limitations of the invention described herein, as well as any additional or optional ingredients, components, or limitations described herein or otherwise useful.

Nail Composition Set

According to the present invention, a nail composition set comprising at least one color coat comprising at least one acrylic latex and water, and at least one primer based on compound(s) other than water are provided. The nail enamel composition set of the present invention can optionally further comprise at least one topcoat. "Nail" as used herein includes fingernails as well as toenails.

For example, a nail composition set comprising at least one primer, at least one color coat and at least one topcoat are provided. However, the topcoat is optional. Thus, nail composition sets comprising at least one primer, at least one color coat and at least one top coat are provided by the present invention.

The nail composition set can also comprise at least one primer and at least one color coat.

It should be understood that each coat or layer in the nail composition set, itself, can comprise one or more layers of each composition. Thus, the at least one primer can comprise one or more primer layers; the at least one color coat can comprise one or more color coat layers; and the at least one topcoat can comprise one or more topcoat layers. Preferably, each primer, color coat and topcoat contains three or fewer layers or compositions, more preferably two or fewer layers or compositions, and most preferably a single layer or composition.

According to the present invention, the color coat and topcoat of the nail composition set can be any suitable composition for application to nails. For example, the topcoat(s) can be a shine layer and/or a protective layer. The color coat(s) can be a nail polish composition(s) as long as it contains an acrylic latex and water.

During application of the nail composition set, the primer is applied to the nail. The, the color coat is applied to the primer. Then, if used, the topcoat is applied to the color coat. In this manner, a nail composition comprising a primer, a color coat and a topcoat (optional) can be prepared on a nail.

Primer

According to the present invention, a primer for application to nails is provided. In accordance with the present invention, the primer is based on at least one compound other than an acrylic latex. Preferably, the at least one compound other than an acrylic latex is a cellulose compound such as nitrocellulose or a polyurethane such as a water-based polyurethane dispersion. "Based on" means that the primer contains at least 30%, preferably at least 50%, and preferably at least 75% by weight with respect to the entire weight of the primer of active material of the compound other than acrylic latex. "Active material" means the compound other than acrylic latex itself; so, for example, an aqueous dispersion of polyurethane contains water and a certain amount of polyurethane (depending upon the dispersion).

Suitable polyurethanes are disclosed in U.S. Pat. No. 7,445,770 and/or U.S. Pat. No. 7,452,770, the entire contents of both of which are hereby incorporated by reference. For example, suitable polyurethanes include aqueous polyurethane dispersions including the reaction products of:

A) a prepolymer according to the formula:

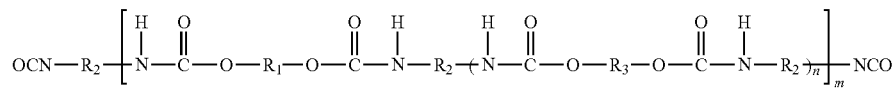

wherein $R_1$ represents a bivalent radical of a dihydroxyl functional compound, $R_2$ represents a hydrocarbon radical of an aliphatic or cycloaliphatic polyisocyanate, $R_3$ represents a radical of a low molecular weight diol, optionally substituted with ionic groups, n is from 0 to 5, and m is >1;

B) at least one chain extender according to the formula: $H_2N$—$R_4$—$NH_2$ wherein $R_4$ represents an alkylene or alkylene oxide radical not substituted with ionic or potentially ionic groups; and C) at least one chain extender according to the formula: $H_2N$—$R_5$—$NH_2$ wherein $R_5$ represents an alkylene radical substituted with ionic or potentially ionic groups.

Suitable dihydroxyl compounds for providing the bivalent radical $R_1$ include those having two hydroxy groups and having number average molecular weights of from about 700 to about 16,000, and preferably from about 750 to about 5000. Examples of the high molecular weight compounds include polyester polyols, polyether polyols, polyhydroxy polycarbonates, polyhydroxy polyacetals, polyhydroxy polyacrylates, polyhydroxy polyester amides, polyhydroxy polyalkadienes and polyhydroxy polythioethers. The polyester polyols, polyether polyols and polyhydroxy polycarbonates are preferred. Mixtures of various such compounds are also within the scope of the present invention.

Suitable polyisocyanates for providing the hydrocarbon radical $R_2$ include organic diisocyanates having a molecular weight of from about 112 to 1,000, and preferably from about 140 to 400. Preferred diisocyanates are those represented by the general formula $R_2(NCO)_2$ indicated above in which $R_2$ represents a divalent aliphatic hydrocarbon group having from 4 to 18 carbon atoms, a divalent cycloaliphatic hydrocarbon group having from 5 to 15 carbon atoms, a divalent araliphatic hydrocarbon group having from 7 to 15 carbon atoms or a divalent aromatic hydrocarbon group having 6-15 carbon atoms. Examples of the organic diisocyanates which are suitable include tetramethylene diisocyanate, 1,6-hexamethylene diisocyanate, dodecamethylene diisocyanate, cyclohexane-1,3- and -1,4-diisocyanate, 1-isocyanato-3-isocyanatomethyl-3,5,5-trimethylcyclohexane (isophorone diisocyanate or IPDI), bis-(4-isocyanatocyclohexyl)-methane, 1,3- and 1,4-bis(isocyanatomethyl)-cyclohexane, bis-(4-isocyanato-3-methyl-cyclohexyl)-methane, isomers of toluene diisocyanate (TDI) such as 2,4-diisocyanatotoluene, 2,6-diisocyanatotoluene, mixtures of these isomers, hydrogenated TDI, 4,4'-diisocyanato diphenyl methane and its isomeric mixtures with 2,4'- and optionally 2,2'-diisocyanato diphenylmethane, and 1,5-diisocyanato naphthalene. Mixtures of diisocyanates can, of course, be used. Preferred diisocyanates are aliphatic and cycloaliphatic diisocyanates. Particularly preferred are 1,6-hexamethylene diisocyanate and isophorone diisocyanate.

"Low molecular weight diols" in the context of $R_3$ means diols having a molecular weight from about 62 to 700, preferably 62 to 200. They may contain aliphatic, alicyclic or aromatic groups. Preferred compounds contain only aliphatic groups. The low molecular weight diols having up to about 20 carbon atoms per molecule include ethylene glycol, diethylene glycol, propane 1,2-diol, propane 1,3-diol, butane 1,4-diol, butylene 1,3-glycol, neopentyl glycol, butyl ethyl propane diol, cyclohexane diol, 1,4-cyclohexane dimethanol, hexane 1,6-diol, bisphenol A (2,2-bis(4-hydroxyphenyl) propane), hydrogenated bisphenol A (2,2-bis(4-hydroxycyclohexyl)propane), and mixtures thereof. Optionally, the low molecular weight diols may contain ionic or potentially ionic groups. Suitable lower molecular weight diols containing ionic or potentially ionic groups are those disclosed in U.S. Pat. No. 3,412,054, the contents of which is hereby incorporated by reference. Preferred compounds include dimethylol butanoic acid (DMBA), dimethylol propionic acid (DMBA) and carboxyl-containing caprolactone polyester diol. If lower molecular weight diols containing ionic or potentially ionic groups are used, they are preferably used in an amount such that <0.30 meq of COOH per gram of polyurethane in the polyurethane dispersion are present.

The prepolymer is chain extended using two classes of chain extenders. First, compounds having the formula: $H_2N-R_4-NH_2$ wherein $R_4$ represents an alkylene or alkylene oxide radical not substituted with ionic or potentially ionic groups. Alkylene diamines include hydrazine, ethylenediamine, propylenediamine, 1,4-butylenediamine and piperazine. The alkylene oxide diamines include 3-{2-[2-(3-aminopropoxy)ethoxy]ethoxy}propylamine (also known as dipropylamine diethyleneglycol or DPA-DEG available from Tomah Products, Milton, Wis.), 2-methyl-1,5-pentanediamine (Dytec A from DuPont), hexane diamine, isophorone diamine, and 4,4-methylenedi-(cyclohexylamine), and the DPA-series ether amines available from Tomah Products, Milton, Wis., including dipropylamine propyleneglycol, dipropylamine dipropyleneglycol, dipropylamine tripropyleneglycol, dipropylamine poly(propylene glycol), dipropylamine ethyleneglycol, dipropylamine poly(ethylene glycol), dipropylamine 1,3-propane diol, dipropylamine 2-methyl-1,3-propane diol, dipropylamine 1,4-butane diol, dipropylamine 1,3-butane diol, dipropylamine 1,6-hexane diol and dipropylamine cyclohexane-1,4-dimethanol. Mixtures of the listed diamines may also be used.

The second class of chain extenders are compounds having the formula: $H_2N-R_5-NH_2$ wherein $R_5$ represents an alkylene radical substituted with ionic or potentially ionic groups. Such compounds have an ionic or potentially ionic group and two groups that are reactive with isocyanate groups. Such compounds contain two isocyanate-reactive groups and an ionic group or group capable of forming an ionic group. The ionic group or potentially ionic group can be selected from the group consisting of ternary or quaternary ammonium groups, groups convertible into such a group, a carboxyl group, a carboxylate group, a sulfonic acid group and a sulfonate group. The at least partial conversion of the groups convertible into salt groups of the type mentioned may take place before or during the mixing with water. Specific compounds include diaminosulfonates, such as for example the sodium salt of N-(2-aminoethyl)-2-aminoethane sulfonic acid (AAS) or the sodium salt of N-(2-aminoethyl)-2-aminopropionic acid.

Commercially available examples of such latexes include, but are not limited to, aqueous polyurethane dispersions comprising a reaction product of a prepolymer comprising a dihydroxyl compound, a polyisocyanate, and a low molecular weight diol and at least two diamine compounds and wherein the composition is substantially free of triethanolamine stearate such as, for example, those sold under the BAYCUSAN® name by Bayer such as, for example, BAYCUSAN® C1000 (polyurethane-34), BAYCUSAN® C1001 (polyurethane-34), BAYCUSAN® C1003 (polyurethane-32), and BAYCUSAN® C1004 (polyurethane-35).

Other examples of suitable examples of polyurethane dispersions include, but are not limited to, other polyurethanes such as, for example, polyurethane 4, 11, 14, 15, 18, 19, 25, 26, 32, 33, 34, 35, 48 etc.

BAYCUSAN® C1001 (polyurethane-34) is most preferred.

Preferably, the compound other than acrylic latex is present in the inventive primer compositions in amounts of active material generally at least 30%, preferably at least 50%, and preferably at least 75% by weight, based on the total weight of the composition, including all ranges and subranges in between Preferably, total water content present in the inventive primer compositions is in amounts generally ranging from about 30% to about 90%, preferably from about 40% to about 75%, and preferably from about 50% to about 60%, by weight, based on the total weight of the composition, including all ranges and subranges in between.

According to particularly preferred embodiments of the present invention, the primer composition further comprises one or more ingredients selected from the group consisting of water-soluble film forming agents, coalescent agents and plasticizers.

According to particularly preferred embodiments of the present application, compositions further comprising at least one water-soluble film forming agent are provided. A "water-soluble film forming agent" is a polymer which can be dissolved in an aqueous phase.

Specific examples of suitable water-soluble film forming agents include, but are not limited to, proteins, such as proteins of plant origin, such as, for example, wheat or soya proteins; or proteins of animal origin, such as keratins, for example keratin hydrolysates and sulfonic keratins; acrylic polymers or copolymers, such as, for example, polyacrylates or polymethacrylates; vinyl polymers, such as, for example, polyvinylpyrrolidones, copolymers of methyl vinyl ether and of maleic anhydride, the copolymer of vinyl acetate and of crotonic acid, copolymers of vinylpyrrolidone and of vinyl acetate, copolymers of vinylpyrrolidone and of caprolactam, or polyvinyl alcohol; gums arabic, guar gum, xanthan derivatives or karaya gum; alginates and carrageenans; glycoaminoglycans, hyaluronic acid and its derivatives; shellac resin, gum sandarac, dammars, elemis or copals; muccopolysaccharides, such as chondroitin sulfates; and their mixtures.

According to preferred embodiments, the at least one water-soluble film forming agent, if present, is present in the compositions of the present invention in an amount of active material ranging from about 0.01 to about 30% by weight, more preferably from about 0.1 to about 20% by weight, and most preferably from about 1 to about 10% by weight, based on the total weight of the composition, including all ranges and subranges within these ranges.

According to particularly preferred embodiments of the present application, primer compositions further comprising at least one plasticizer and/or coalescent are provided. Plasticizers are additives used to optimize the mechanical properties of the films. They tend to reduce the Glass Transition Temperature (Tg) and increase the softness and flexibility of the films. Coalescents are additives used to aid the coalescence of the latex particles, and hence assisting the film formation process.

Preferably, the plasticizer has a distribution coefficient D of less than or equal to 0.1. The distribution coefficient can be determined in accordance with the teaching of "A method to predict the distribution coefficient of coalescing agents between latex particles and the water phase," *Progress in Organic Coatings*, vol. 30, 1997, pp. 173-177, the disclosure of which is specifically incorporated by reference herein.

Preferably, the plasticizer has a boiling point measured at ambient pressure of less than or equal to 285° C., preferably less than or equal to 270° C., and preferably less than or equal to 250° C. In the present specification, the boiling point values are to he considered accurate to ±2° C. owing to the uncertainties of boiling point measurement.

Any plasticizing agent typically found in nail polish compositions can be used. Examples of suitable plasticizers include, but are not limited to, glycols and their ester derivatives, esters of acids, in particular carboxylic acids, such as citrates, adipates, carbonates, tartrates, phosphates or sebacates, oxyethylenated derivatives, such as oxyethylenated oils, and their mixtures. For example, suitable plasticizing agents include, but are not limited to, diisobutyl adipate, the ester of teributyl acid and 2,2,4-trimethylpentane-1,3-diol, diethyl adipate, diethyl phthalate, dibutyl phthalate, dioctyl phthalate, butyl 2-ethylhexyl phthalate, dimethyl sebacate, dibutyl sebacate, ethyl stearate, 2-ethylhexyl palmitate, dipropylene glycol n-butyl ether, tributyl phosphate, tributoxyethyl phosphate, tricresyl phosphate, triphenyl phosphate, glycerol triacetate, butyl stearate, butyl glycolate, benzyl benzoate, butyl acetyltricinoleate, glyceryl acetyltricinoleate, dibutyl phthalate, diisobutyl phthalate, dioctyl phthalate, dimethoxyethyl phthalate, diamyl phthalate, triethyl citrate, tributyl citrate, tributyl acetylcitrate, tri(2-ethylhexyl) acetylcitrate, dibutyl tartrate, camphor, and mixtures thereof.

In accordance with preferred embodiments, the plasticizer, if present, is preferably present in the primer composition in an amount of from 0.1% to 25% by weight, preferably from 0.25% to 22% by weight, preferably from 0.5 to 20% by weight, of the total weight of the composition, including all ranges and subranges therebetween.

According to particularly preferred embodiments of the present application, primer compositions further comprising at least one coalescent agent are provided. The coalescent agent promotes the coalescence of the polymer(s) in the composition.

Preferably, the coalescent agent has a distribution coefficient D' of greater than or equal to 0.5, measured in accordance with the above-referenced "A method to predict the distribution coefficient of coalescing agents between latex particles and the water phase," *Progress in Organic Coatings*, vol. 30, 1997, pp. 173-177.

Preferably, the coalescent agent has a boiling point measured at ambient pressure ranging from 90° C. to 180° C., preferably from 150° C. to 180° C.

Any coalescent agent typically found in nail polish compositions can be used. Examples of suitable plasticizers include, but are not limited to, propylene glycol n-butyl ether, dipropylene glycol dimethyl ether, propylene glycol methyl ether acetate, propylene glycol propyl ether, methyl lactate, ethyl lactate, isopropyl lactate, and mixtures thereof.

In accordance with preferred embodiments, the coalescent agent, if present, is preferably present in the primer composition in an amount of from 0.1% to 25% by weight, preferably from 1% to 15% by weight, preferably from 3 to 10% by weight, of the total weight of the composition, including all ranges and subranges therebetween.

Color Coat

According to the present invention, a color coat for application to nails is provided. In accordance with the present invention, the color coat comprises at least one acrylic latex. Also in accordance with the present invention, the color coat comprises at least one colorant.

"Latex" as used herein encompasses both "latex" and "pseudolatex," and means colloidal dispersions of polymer particles in an aqueous liquid phase.

"Latex" is generally obtained by suspension or emulsion polymerization or copolymerization of monomers according to processes that are well known to those of ordinary skill in the art. Such monomers may be chosen in particular from styrene, butadiene, acrylonitrile, chloroprene, vinyl acetate, urethanes, isoprene, isobutylene, and acrylic or methacrylic acid, maleic acid, crotonic acid or itaconic acid or esters or amides thereof.

"Pseudolatex" denotes a dispersion consisting of generally spherical particles of a polymer, these particles being obtained by dispersing the polymer in a suitable aqueous phase.

Latex and pseudolatex have film-forming properties that are advantageous for imparting adhesive properties to the primer. That is, latex and pseudolatex aid in adhering the primer and, thus, the nail composition to the nail.

Specific examples of types of latexes and pseudolatexes as well as specific examples of latexes and pseudolatexes include:

Synthetic polymers of the polycondensate type or of the free-radical type;

Acrylic polymers resulting from the copolymerization of monomers chosen from the esters and/or amides of acrylic acid or of methacrylic acid. As examples of monomers of ester type, mention may be made of methyl methacrylate, ethyl methacrylate, butyl methacrylate, isobutyl methacrylate, 2-ethylhexyl methacrylate and lauryl methacrylate. As examples of monomers of amide type, mention may be made of N-t-butylacrylamide and N-t-octylacrylamide.

Acrylic polymers obtained by copolymerization of ethylenically unsaturated monomers containing hydrophilic groups, preferably of nonionic nature, such as hydroxyethyl acrylate, 2-hydroxypropyl acrylate, hydroxyethyl methacrylate and 2-hydroxypropyl methacrylate;

Vinyl polymers resulting from the homopolymerization or copolymerization of monomers chosen from vinyl esters, styrene or butadiene. As examples of vinyl esters, mention may be made of vinyl acetate, vinyl neodecanoate, vinyl pivalate, vinyl benzoate and vinyl t-butylbenzoate.

Acrylic/silicone copolymers;

Bimodal film forming agents which form a bimodal interpenetrating network containing multiple functionalities (for example, cationic and anionic functionalities) which is reversibly cross-linked at least partially through the multiple functionalities are disclosed in PCT patent application nos. WO 05/087191 and WO 06/028931, and corresponding U.S.

provisional application Nos. 60/551,658, 60/606,985, and 60/627,224, the entire contents of all of which are hereby incorporated by reference in their entirety. Suitable bimodal film forming agents include, but are not limited to, film forming agents having both cationic and anionic functionalities. According to particularly preferred embodiments of the present invention, the bimodal film forming agent comprises at least one acrylic acid-based, (meth)acrylic acid-based, acrylate-based or (meth)acrylate-based monomer having anionic and/or cationic functionalities. Suitable polymers or copolymers include, but are not limited to, polymers comprising polyacrylates such as those identified in the International Cosmetic Ingredient Dictionary and Handbook (9.sup.th ed. 2002) such as, for example, polyacrylate-1, polyacrylate-2, polyacrylate-3, polyacrylate-4 . . . polyacrylate-16, polyacrylate-17, polyacrylate-18, polyacrylate-19 . . . , etc. Such (co)polymers, or similar (co)polymers, can be combined individually or with other (co)polymers in such a way to form suitable bimodal film forming agents having both cationic and anionic functionalities. According to particularly preferred embodiments, the bimodal film forming agent is selected from the group consisting of polymers consisting of polyacrylate-21 and acrylates/dimethylaminoethylmethacrylate copolymer (marketed under the name Syntran PC 5100 by Interpolymer), polyacrylate-16 (marketed under the name Syntran PC 5112 by Interpolymer), polyacrylate-18 and polyacrylate-19 (marketed under the name Syntran PC 5107 by Interpolymer), and polyacrylate-18 and polyacrylate-1 g (marketed under the name Syntran PC 5117 by Interpolymer). The bimodal film forming agent containing polyacrylate-21 and acrylates/dimethylaminoethylmethacrylate copolymer (Syntran PC 5100) and polyacrylate-16 (Syntran PC 5112) are particularly preferred.

Representative examples of suitable latexes include acrylic copolymer dispersions sold under the names Neocryl XK-90® (INCI name: acrylic/styrene copolymer), Neocryl A-1070® (INCI name: acrylic/styrene copolymer), Neocryl A-1090® (INCI name: acrylic/styrene copolymer), Neocryl BT-62® (INCI name: acrylic/styrene copolymer), Neocryl A-1079® (INCI name: acrylic/styrene copolymer) and Neocryl A-523® (INCI name: acrylic/styrene copolymer) by the company Avecia-Neoresins, Dow Latex 432® (INCI name: Styrene/Acrylates Copolymer) by the company Dow Chemical, Daitosol 5000 AD® (INCI name: acrylates copolymer) by the company Daito Kasey Kogyo.

Further examples of latex polymers useful in the present invention include (meth)acrylate copolymers such as, for example, acrylate copolymers (acrylates/ethylhexyl acrylate copolymer, sold by Daito Kasei under the tradename Daitosol 5000SJ), butyl acrylate/hydroxypropyl dimethicone acrylate copolymers (Granacrysil BAS by Grant Industries, Inc.), acrylates/C12-C22 alkylmethacrylate copolymers (Allianz OPT by ISP), isododecane and acrylates copolymers (Giovarez AC-5099M by Phoenix), and acrylates/octylacrylamide copolymers (Dermacryl-79 by National Starch & Chemical Company).

Finally, suitable examples of latexes/pseudolatexes can be found, for example, in U.S. patent application Ser. Nos. 61/541,173, 61/542,131, and 61/542,136, U.S. patent application publication no. 2008/0081054, and U.S. Pat. Nos. 5,538,717, 5,672,647, 6,297,950 and 6,372,201, the entire contents of all of which are hereby incorporated by reference.

In accordance with preferred embodiments, the acrylic latex is preferably present in the color coat in an amount of from 15% to 55% by weight, preferably 20% to 50% by weight, preferably from 35% to 45% by weight, of the total weight of the composition, including all ranges and subranges therebetween.

Any colorant typically found in nail polish compositions can be used. Suitable colorants include, but are not limited to, lipophilic dyes, pigments and pearlescent agents, and their mixtures.

Suitable examples of fat-soluble dyes are, for example, Sudan red, DC Red 17, DC Green 6, β-carotene, soybean oil, Sudan brown, DC Yellow 11, DC Violet 2, DC Orange 5 and quinoline yellow.

Suitable pigments can be white or colored, inorganic and/or organic and coated or uncoated. Mention may be made, for example, of inorganic pigments such as titanium dioxide, optionally surface treated, zirconium or cerium oxides and iron or chromium oxides, manganese violet, ultramarine blue, chromium hydrate and ferric blue. Mention may also be made, among organic pigments, of carbon black, pigments of D & C type and lakes based on cochineal carmine or on barium, strontium, calcium or aluminum, such as D&C Red No. 10, 11, 12, and 13, D&C Red No. 7, D&C Red No. 5 and 6, and D&D Red No. 34, as well as lakes such as D&C Yellow Lake No. 5 and D&C Red Lake No. 2.

Suitable pearlescent pigments can be chosen from, for example, white pearlescent pigments, such as mica covered with titanium oxide or with bismuth oxychloride, colored pearlescent pigments, such as titanium oxide-coated mica with iron oxides, titanium oxide-coated mica with in particular ferric blue or chromium oxide, or titanium oxide-coated mica with an organic pigment of the abovementioned type, and pearlescent pigments based on bismuth oxychloride.

In accordance with preferred embodiments, the colorant is preferably present in the color coat in an amount of from 0.01% to 20% by weight, preferably from 0.1% to 15% by weight, preferably from 0.5 to 10% by weight, of the total weight of the composition, including all ranges and subranges therebetween.

The color coat can be a UV gel nail composition or a conventional nail composition, if desired.

Examples of suitable UV gel nail compositions can be found, for example, in U.S. Pat. Nos. 5,435,994, and 5,456,905, and US patent application publication nos. 2011/082228, 2011/081306, 2011/060065, 2011/182838, 2011/274633. Further, suitable compositions can be found in U.S. Ser. 61/476,339, the entire contents of which is hereby incorporated by reference in its entirety.

Examples of suitable conventional solvent-based compositions can be found, for example, in U.S. Pat. Nos. 7,455,831, 7,025,953, 6,555,096, 6,372,201, 6,333,025, and 6,254,878, the entire contents of all of which are hereby incorporated by reference in their entireties.

Topcoat

According to preferred embodiments of the invention nail composition sets, these sets can optionally further contain at least one topcoat. The topcoat is thus optional in the nail composition set of the present invention. However, it is preferred if the topcoat is present. In accordance with these preferred embodiments, any topcoat suitable for application to nails as a topcoat can be used. That is, the topcoat employed in the nail compositions of the present invention is not limited: as long as the topcoat is suitable for application to nails, it is suitable for the nail composition set of the present invention. Typically, topcoats provide shine and/or protection to color coats of nail composition set.

Auxiliaries/Additives

The primer, the color coat, and the topcoat of the layers in the nail composition set of the present invention may additionally comprise an additive or auxiliary commonly used in cosmetic compositions and known to a person skilled in the art as being capable of being incorporated into a nail polish or varnish composition. Such additives or auxiliaries may be chosen from thickeners, coalescents, preservatives, fragrances, oils, waxes, surfactants, antioxidants, agents for combating free radicals, spreading agents, wetting agents, dispersing agents, antifoaming agents, neutralizing agents, stabilizing agents, active principles chosen from essential oils, UV screening agents, sunscreens, moisturizing agents, vitamins, proteins, ceramides, plant extracts, fibers, and the like, and their mixtures.

A person skilled in the art will take care to select the optional additional additives and/or the amount thereof such that the advantageous properties of the composition according to the invention are not, or are not substantially, adversely affected by the envisaged addition.

These substances may be selected variously by the person skilled in the art in order to prepare a composition which has the desired properties, for example, consistency or texture.

These additives may be present in the composition in a proportion from 0% to 99% (such as from 0.01% to 90%) relative to the total weight of the composition and further such as from 0.1% to 50% (if present), including all ranges and subranges therebetween.

Needless to say, the composition of the invention should be cosmetically or dermatologically acceptable, i.e., it should contain a non-toxic physiologically acceptable. The composition may be in any galenic form normally employed in the cosmetic and dermatological fields which is suitable for topical administration onto nails.

According to preferred embodiments of the present invention, methods of making up or protecting nails comprising applying to the nails at least one primer and at least one color coat to nails in an amount sufficient to makeup or protect the nails are provided. According to preferred embodiments, at least one topcoat is further applied to the nails in the following order: nail/primer/color coat/topcoat (if applied).

"Making up" as used herein means to provide decoration (for example, color) to the nail. "Protecting" as used herein means to inhibit damage to the nail (for example, chipping) by providing a protective layer on the nail.

In accordance with preferred embodiments of the preceding methods, at least one primer and at least one color coat are applied topically to the nails of a person in need of (desirous) the desired making up or protection in an amount sufficient to achieve the desired result. The compositions may be applied to the desired area as needed.

According to preferred embodiments, methods of inhibiting a color coat comprising at least one acrylic latex and water from staining a nail to which the color coat is applied comprising applying to the nail at least one primer based on compound(s) other than acrylic latex prior to applying the color coat to the nail are provided. According to preferred embodiments, at least one topcoat is further applied to the nails in the following order: nail/primer/color coat/topcoat (if applied).

According to preferred embodiments of the present invention, a kit for a nail composition set comprising at least one primer composition are also provided. Preferably, the kit further comprises one or more of the following compositions: a topcoat composition; a color coat composition; a conventional nail polish composition; and/or a UV gel composition. Preferably, the kit further comprise instructions for removing a nail composition by removing the primer composition to effect removal of the nail composition.

The compositions according to the invention can be manufactured by known processes used generally in the cosmetics or dermatological field.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

EXAMPLES

Example 1

Color Coat Base Formula (A)

| INCI | Trade Name | % (RM) |
|---|---|---|
| STYRENE/ACRYLATES/ AMMONIUM METHACRYLATE COPOLYMER (and) SODIUM LAURYL SULFATE (and) SODIUM LAURETH SULFATE | Syntran 5620 | 61 |
| AMMONIUM ACRYLATES COPOLYMER | VINYSOL 1086WP | 22 |
| STYRENE/ACRYLATES COPOLYMER | Joncryl 77 | 5.32 |
| POLYURETHANE-34 | BAYCUSAN C 1001 | 2.85 |
| PPG-2 BUTYL ETHER | DOWANOL DPNB | 1 |
| Propylene Glycol Dibenzoate | LEXFEEL SHINE | 4.59 |
| TRIBUTYL CITRATE | SCANDINOL SP 21 | 1.24 |
| Phenoxyethanol | PHENOXETOL | 1 |
| Caprylyl Glycol | DERMOSOFT OCTIOL | 1 |
| TOTAL | | 100 |

Example 2

Color Coat Formula (B)

| Color Coat Formula (B) | | | |
|---|---|---|---|
| INCI | Trade Name | Supplier | % RM |
| Base Formula (A) | | | 92 |
| YELLOW 5 LAKE | N.A | SUN CHEMICAL | 6 |
| AMINOMETHYL PROPANEDIOL | AMPD ULTRA PC | ANGUS (DOW CHEMICAL) | 2 |
| TOTAL | | | 100 |

Example 3

Various Basecoat Formulations

| Ingredient | | Base coat 1 | Base coat 2 | Base coat 3 | Base coat 4 | Base coat 5 |
|---|---|---|---|---|---|---|
| INCI | Trade Name | | | | | |
| STYRENE/ACRYLATES/AMMONIUM METHACRYLATE COPOLYMER (and) SODIUM LAURYL SULFATE (and) SODIUM LAURETH SULFATE | Syntran 5620 | 61 | | | | |
| AMMONIUM ACRYLATES COPOLYMER | VINYSOL 1086WP | 22 | | | | |
| STYRENE/ACRYLATES COPOLYMER | Joncryl 77 | 5.32 | | | | |
| PPG-2 BUTYL ETHER | DOWANOL DPNB | 1 | | | | |
| Propylene Glycol Dibenzoate | LEXFEEL SHINE | 4.59 | | | | |
| ACRYLATES/ETHYLHEXYL ACRYLATE COPOLYMER | DAITOSOL 5000 SJ | | | 97.5 | | |
| ACRYLATES COPOLYMER | Luviflex SOFT | | 92.5 | | | |
| TRIBUTYL CITRATE | SCANDINOL SP 21 | 1.24 | 5 | | | |
| POLYURETHANE-34 | BAYCUSAN C 1001 | 2.85 | | | 97.5 | |
| SIMETHICONE | XIAMETER AFE-0100 AF EMUL FG | | 0.5 | 0.5 | 0.5 | |
| Phenoxyethanol | PHENOXETOL | 1 | 1 | 1 | 1 | |
| Caprylyl Glycol | DERMOSOFT OCTIOL | 1 | 1 | 1 | 1 | |
| Ethyl Acetate | | | | | | 35-45 |
| Butyl Acetate | | | | | | 25-30 |
| Nitrocellulose | | | | | | 10-15 |
| ADIPIC ACID/NEOPENTYL GLYCOL/TRIMELLITIC ANHYDRIDE COPOLYMER | | | | | | 5-10 |
| ACETYL TRIBUTYL CITRATE | | | | | | 5-10 |
| ISOPROPYL ALCOHOL | | | | | | ~5 |
| Other Additives | | | | | | 0-10 |
| Total % | | 100 | 100 | 100 | 100 | 100 |

Example 4

Sensory Testing

Basecoat compositions 1-5 above were evaluated as follows.

Basecoats 1-3 were based on acrylate copolymers. Basecoat 4 was based on polyurethane. Basecoat 5 was based on nitrocellulose.

Two studies were conducted.

In the first study, one layer of basecoat (1-5) of each composition was applied on different fingers, and was allowed to dry 1-2 minutes. Subsequently, two coats of Color Coat Formula (B) were applied to each finger, then allowed to dry for 1-2 minutes. The nail polish was then worn for 2 days. After 2 days, the nail polish layers were removed by peeling off in warm water. The staining condition of the nails was evaluated visually.

In the second study, the same procedure was followed, except the nail polish was worn for 4 days.

From both study 1 and study 2, it was found that when the basecoat and color coat shared acrylate copolymer chemistry, nail staining was more pronounced (basecoats 1-3). In contrast, if the basecoat and color coat did not share acrylate copolymer chemistry (basecoats 4 and 5), staining behavior was reduced. It was thus found that for color coats based on acrylic latex, use of polyurethane (basecoat 4) or nitrocellulose (basecoat 5) significantly prevents staining of the nail by the color coat. The studies are summarized as follows:

| | Comparative System 1 | Comparative System 2 | Comparative System 3 | Inventive System 4 | Inventive System 5 |
|---|---|---|---|---|---|
| Base Coat | Base Coat 1 | Base Coat 2 | Base Coat 3 | Base Coat 4 | Base Coat 5 |
| Base Coat Key Chemistry | ACRYLATE COPOLYMER | ACRYLATE COPOLYMER | ACRYLATES/ETHYLHEXYL ACRYLATE COPOLYMER | Polyurethane | Nitrocellulose |
| Color Coat | Color Coat Formula (B) from Above Table | | | | |
| Color Coat Key Chemistry | ACRYLATE COPOLYMER | | | | |
| Application 1 Base Coat 2 Color Coat Wear 2 days | Staining Observed | Staining Observed | Staining Observed | No/Minimal Staining | No/Minimal Staining |

-continued

| | Comparative System 1 | Comparative System 2 | Comparative System 3 | Inventive System 4 | Inventive System 5 |
|---|---|---|---|---|---|
| Application 2 Base Coat 2 Color Coat Wear 4 days | Staining Observed | Staining Observed | Minimal Staining | No/Minimal Staining | No/Minimal Staining |

What is claimed is:

1. A nail composition set comprising (a) at least one primer based on comprising at least 75% by weight of at least one polyurethane, and (b) at least one color coat comprising at least one acrylic latex, at least one colorant and water; wherein the primer comprises at least one aqueous polyurethane dispersion comprising a reaction product of:

a prepolymer according to the following formula:

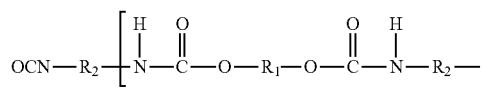

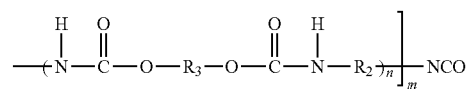

wherein $R_1$ represents a dihydroxyl compound having a number average molecular weights of from about 700 to about 16,000, $R_2$ represents a hydrocarbon radical of an aliphatic or cycloaliphatic polyisocyanate, and $R_3$ represents a radical of a low molecular weight diol, n is from 0 to 5, and m is >1;

at least one chain extender according to the formula: $H_2N-R_4-NH_2$ wherein $R_4$ represents an alkylene or alkylene oxide radical not substituted with ionic or potentially ionic groups; and at least one chain extender according to the formula: $H_2N-R_5-NH_2$ wherein $R_5$ represents an alkylene radical substituted with ionic or potentially ionic groups.

2. The nail composition set of claim 1, further comprising at least one topcoat.

3. The nail composition set of claim 1, wherein the color coat is a UV gel composition.

4. The nail composition set of claim 1, wherein the at least one aqueous polyurethane dispersion comprises a reaction product of a prepolymer comprising a dihydroxyl compound, a polyisocyanate, and a low molecular weight diol and at least two diamine compounds and wherein the composition is substantially free of triethanolamine stearate.

5. The nail composition set of claim 1, wherein the primer further comprises at least one plasticizer.

6. The nail composition set of claim 1, wherein the polyurethane is present in an amount of 75% to 90% by weight with respect to the total weight of the primer.

7. The nail composition set of claim 4, wherein the polyurethane is present in an amount of 75% to 90% by weight with respect to the total weight of the primer.

8. A method of inhibiting a color coat comprising at least one acrylic latex and water from staining a nail to which the color coat is applied comprising applying to the nail at least one primer comprising at least 75% by weight of at least one polyurethane prior to applying the color coat to the nail; wherein the primer comprises at least one aqueous polyurethane dispersion comprising a reaction product of:

a prepolymer according to the following formula:

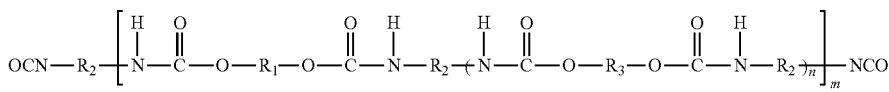

wherein $R_1$ represents a dihydroxyl compound having a number average molecular weights of from about 700 to about 16,000, $R_2$ represents a hydrocarbon radical of an aliphatic or cycloaliphatic polyisocyanate, and $R_3$ represents a radical of a low molecular weight diol, n is from 0 to 5, and m is >1;

at least one chain extender according to the formula: $H_2N-R_4-NH_2$ wherein $R_4$ represents an alkylene or alkylene oxide radical not substituted with ionic or potentially ionic groups; and at least one chain extender according to the formula: $H_2N-R_5-NH_2$ wherein $R_5$ represents an alkylene radical substituted with ionic or potentially ionic groups.

9. The method of claim 8, wherein the at least one aqueous polyurethane dispersion comprises a reaction product of a prepolymer comprising a dihydroxyl compound, a polyisocyanate, and a low molecular weight diol and at least two diamine compounds and wherein the composition is substantially free of triethanolamine stearate.

10. The method of claim 8, wherein the polyurethane is present in an amount of 75% to 90% by weight with respect to the total weight of the primer.

11. The method of claim 9, wherein the polyurethane is present in an amount of 75% to 90% by weight with respect to the total weight of the primer.

12. The method of claim 8, wherein the polyurethane is present in an amount of 75% to 90% by weight with respect to the total weight of the primer.

* * * * *